(12) United States Patent
Yamamoto

(10) Patent No.: US 9,456,738 B2
(45) Date of Patent: Oct. 4, 2016

(54) ENDOSCOPIC DIAGNOSIS SYSTEM

(75) Inventor: Hiroaki Yamamoto, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 577 days.

(21) Appl. No.: 13/283,407

(22) Filed: Oct. 27, 2011

(65) Prior Publication Data

US 2012/0165627 A1    Jun. 28, 2012

(30) Foreign Application Priority Data

Dec. 24, 2010  (JP) ................................ 2010-287566

(51) Int. Cl.
| | |
|---|---|
| A61B 6/00 | (2006.01) |
| A61B 1/04 | (2006.01) |
| A61B 1/06 | (2006.01) |
| A61B 5/1455 | (2006.01) |
| A61B 1/07 | (2006.01) |

(52) U.S. Cl.
CPC ............... *A61B 1/043* (2013.01); *A61B 1/063* (2013.01); *A61B 1/0638* (2013.01); *A61B 1/0653* (2013.01); *A61B 5/14551* (2013.01); *A61B 1/0646* (2013.01); *A61B 1/07* (2013.01)

(58) Field of Classification Search
USPC ........................................ 600/407, 476, 478
See application file for complete search history.

(56) References Cited

U.S. PATENT DOCUMENTS

| | | | |
|---|---|---|---|
| 6,081,740 A * | 6/2000 | Gombrich et al. ........... | 600/424 |
| 6,364,829 B1 * | 4/2002 | Fulghum ...................... | 600/160 |
| 6,465,968 B1 | 10/2002 | Sendai | |
| 7,226,412 B2 * | 6/2007 | Ueno et al. ................... | 600/178 |
| 2004/0215060 A1 | 10/2004 | Ueno et al. | |
| 2006/0178565 A1 * | 8/2006 | Matsui ............... | A61B 1/00009 600/160 |

(Continued)

FOREIGN PATENT DOCUMENTS

| | | | |
|---|---|---|---|
| JP | 2000-189382 A | 7/2000 | |
| JP | 2001-128925 A | 5/2001 | |

(Continued)

OTHER PUBLICATIONS

"Appearance of enhanced tissue features in narrow-band endoscopic imaging" by K. Gono et al. J Biomed. Optics. 9(3). pp. 568-577. 2004.*

(Continued)

*Primary Examiner* — Tse Chen
*Assistant Examiner* — Jason Ip
(74) *Attorney, Agent, or Firm* — McGinn IP Law Group, PLLC

(57) ABSTRACT

An endoscopic diagnosis system includes a first narrowband light source for emitting first narrowband light having a given wavelength range, a second narrowband light source for emitting second narrowband light having a wavelength range different from that of the first narrowband light, a first image sensor for receiving reflected light of the first narrowband light illuminating a subject from the subject to acquire a narrowband light image in a narrowband light observation mode, a second image sensor for receiving first autofluorescence emitted from the subject as the first narrowband light illuminates the subject to acquire a first autofluorescence image in a first autofluorescence observation mode and receiving second autofluorescence emitted from the subject as the second narrowband light illuminates the subject to acquire a second autofluorescence image in a second autofluorescence observation mode.

10 Claims, 8 Drawing Sheets

(56) References Cited

U.S. PATENT DOCUMENTS

| 2007/0041720 | A1 | 2/2007 | Iketani |
| 2007/0160279 | A1* | 7/2007 | Demos .......................... 382/133 |
| 2008/0017787 | A1 | 1/2008 | Okawa et al. |
| 2008/0255426 | A1 | 10/2008 | Iketani |
| 2009/0219384 | A1 | 9/2009 | Iketani et al. |

FOREIGN PATENT DOCUMENTS

| JP | 2005-319213 A | 11/2005 |
| JP | 2007-020728 A | 2/2007 |
| JP | 2007-50106 A | 3/2007 |
| JP | 2007-111151 A | 5/2007 |
| JP | 2008-043383 A | 2/2008 |
| JP | 2008-259722 A | 10/2008 |
| JP | 2010-022700 A | 2/2010 |
| WO | WO 2005-104926 A1 | 11/2005 |

OTHER PUBLICATIONS

European Search Report dated May 30, 2012.
Notification of Reasons for Refusal dated Nov. 27, 2012, with English translation.
Notification of Reasons for Refusal dated Apr. 30, 2013, with English translation.

* cited by examiner

ENDOSCOPIC DIAGNOSIS SYSTEM

BACKGROUND OF THE INVENTION

The present invention relates to an endoscopic diagnosis system for performing narrowband light observation and autofluorescence observation as special light observation.

There is conventionally used an endoscope device wherein white light (normal light) emitted from a light source device is guided to the tip of an endoscope to illuminate a region under observation of a subject, and the reflected light is imaged to acquire a normal light image (white light image) in order to perform normal light observation (white light observation). In recent years, there is used an endoscope device wherein a region under observation of a subject is illuminated by narrowband light (special light) having a given wavelength range, and the reflected light and autofluorescence are imaged to acquire a special light image in order to perform special light observation in addition to normal light observation. See JP 2007-50106 A.

An endoscope device capable of special light observation can readily visualize biological information on, for example, a fine structure of a new blood vessel formed in a mucosa layer or beneath a mucosa layer in a subject's lumen and enhancement of a site of lesion, which is unobtainable from a normal observation image. When, for example, the site to be observed is a cancer-affected region, illuminating a mucosa tissue with blue narrowband light enables observation of fine blood vessels in the superficial layer of a tissue and a fine structure in greater detail and thus permits diagnosis of a site of lesion with an increased accuracy.

As illustrated in a conceptual view of FIG. 11, the electronic endoscope described in JP 2007-50106 A illuminates a site under observation with one kind of excitation light, and images the reflected light thereof with a first sensor (image sensor) having blue filters to obtain a narrowband light image while simultaneously imaging the autofluorescence with a second sensor having green and red filters to obtain an autofluorescence image in special light observation mode.

In the normal light observation mode, white light is allowed to illuminate the site under observation, with a blue filter that only passes excitation light having a wavelength range of 400 nm to 500 nm located in a position off the optical path, and the reflected light thereof is imaged by the first and the second sensor. The process generates a video signal of a normal light image composed of red, green, and blue light consisting of a blue color signal of the first sensor and a green and a red color signal of the second sensor.

In the special light observation mode, a blue filter is positioned on the optical path to allow excitation light having a wavelength range of 400 nm to 500 nm to illuminate the site under observation, and the reflected light thereof and the autofluorescence are imaged by the first and the second sensor. The process simultaneously generates a video signal of a narrowband light image composed of a blue color signal of the first sensor and a video signal of an autofluorescence image composed of a green and a red color signal of the second sensor.

SUMMARY OF THE INVENTION

However, according to the method described in JP 2007-50106 A, whereby a narrowband light image and an autofluorescence image are acquired simultaneously, the excitation light has the same intensity for acquiring both images, but when the excitation light has the same intensity, a high-quality autofluorescence image cannot be obtained because the fluorescence intensity of autofluorescence is feeble. This method had another problem that using a sensor sensitive to blue light to obtain a narrowband light image, i.e., using blue color signals alone can only allow observation of blood vessels lying in a superficial layer.

A first object of the present invention is to provide an endoscopic diagnosis system enabling a high-quality autofluorescence image to be obtained in an endoscopic diagnosis system that acquires a narrowband light image and an autofluorescence image.

A second object of the present invention is to provide an endoscopic diagnosis system enabling observation of blood vessels lying in a superficial to an intermediate layer.

In order to achieve the above-described objects, the present invention provides an endoscopic diagnosis system, comprising:

a first narrowband light source for emitting first narrowband light having a given wavelength range;

a second narrowband light source for emitting second narrowband light having a wavelength range different from that of the first narrowband light;

a first image sensor for receiving reflected light of the first narrowband light illuminating a subject from the subject and acquiring a narrowband light image in a narrowband light observation mode;

a second image sensor for receiving first autofluorescence emitted from the subject as the first narrowband light illuminates the subject to acquire a first autofluorescence image in a first autofluorescence observation mode and receiving second autofluorescence emitted from the subject as the second narrowband light illuminates the subject to acquire a second autofluorescence image in a second autofluorescence observation mode; and a light source controller for increasing emission amounts of the first and the second narrowband light in the first and the second autofluorescence observation mode to emission amounts greater than emission amounts used in the narrowband light observation mode.

According to the present invention, a high-quality autofluorescence image can be obtained by increasing the emission amounts of the first and the second narrowband light (excitation light for autofluorescence observation) in an autofluorescence observation mode so as to be double those used in the narrowband light observation mode. Thus, using the first and the second narrowband light having different wavelength ranges enables selective excitation of only specific autofluorescent substances. In the narrowband light observation mode, blood vessels lying in the superficial to intermediate layer of the subject can be observed by illuminating the subject with white light and the first narrowband light at a given emission ratio.

DETAILED DESCRIPTION OF THE INVENTION

The endoscopic diagnosis system according to the present invention will be described in detail based on the preferred embodiments illustrated in the attached drawings.

Figure 1:
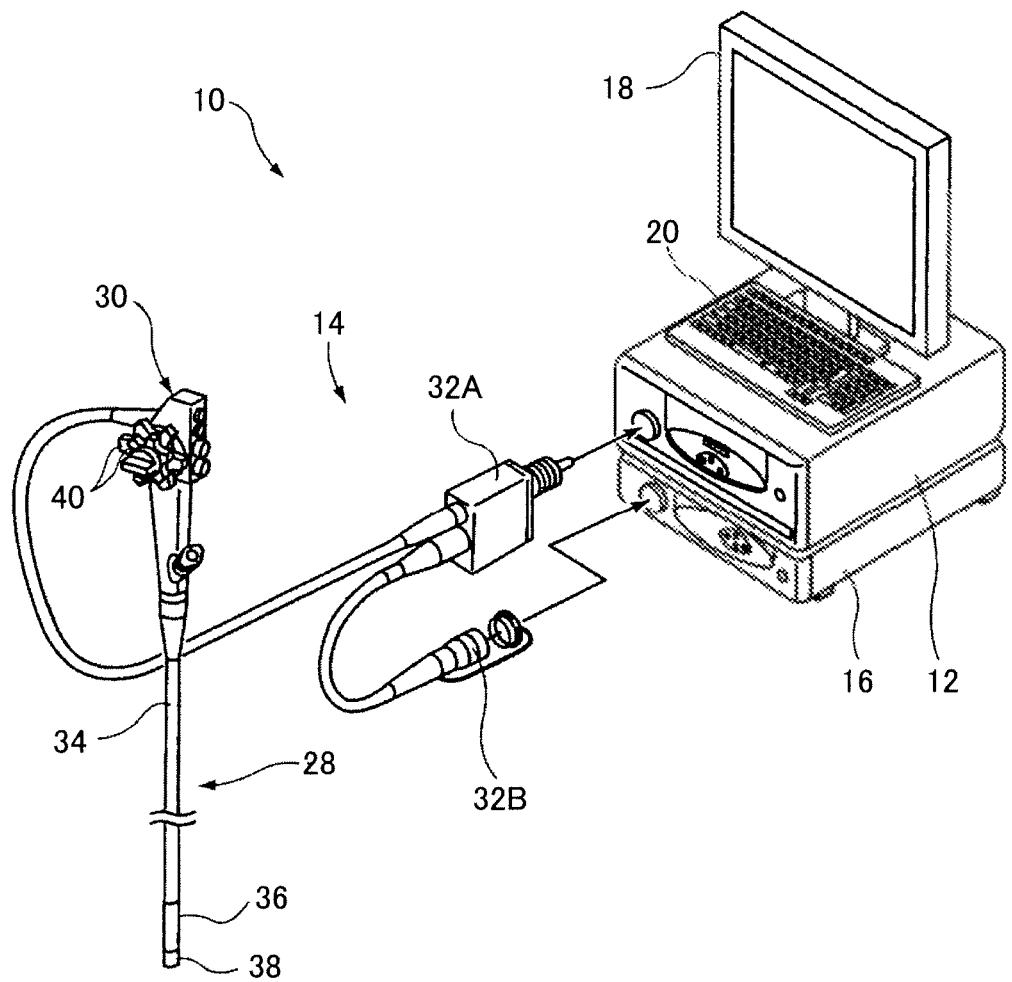
FIG. 1 is an external view of an embodiment illustrating a configuration of the endoscopic diagnosis system according to the invention.
Figure 2:
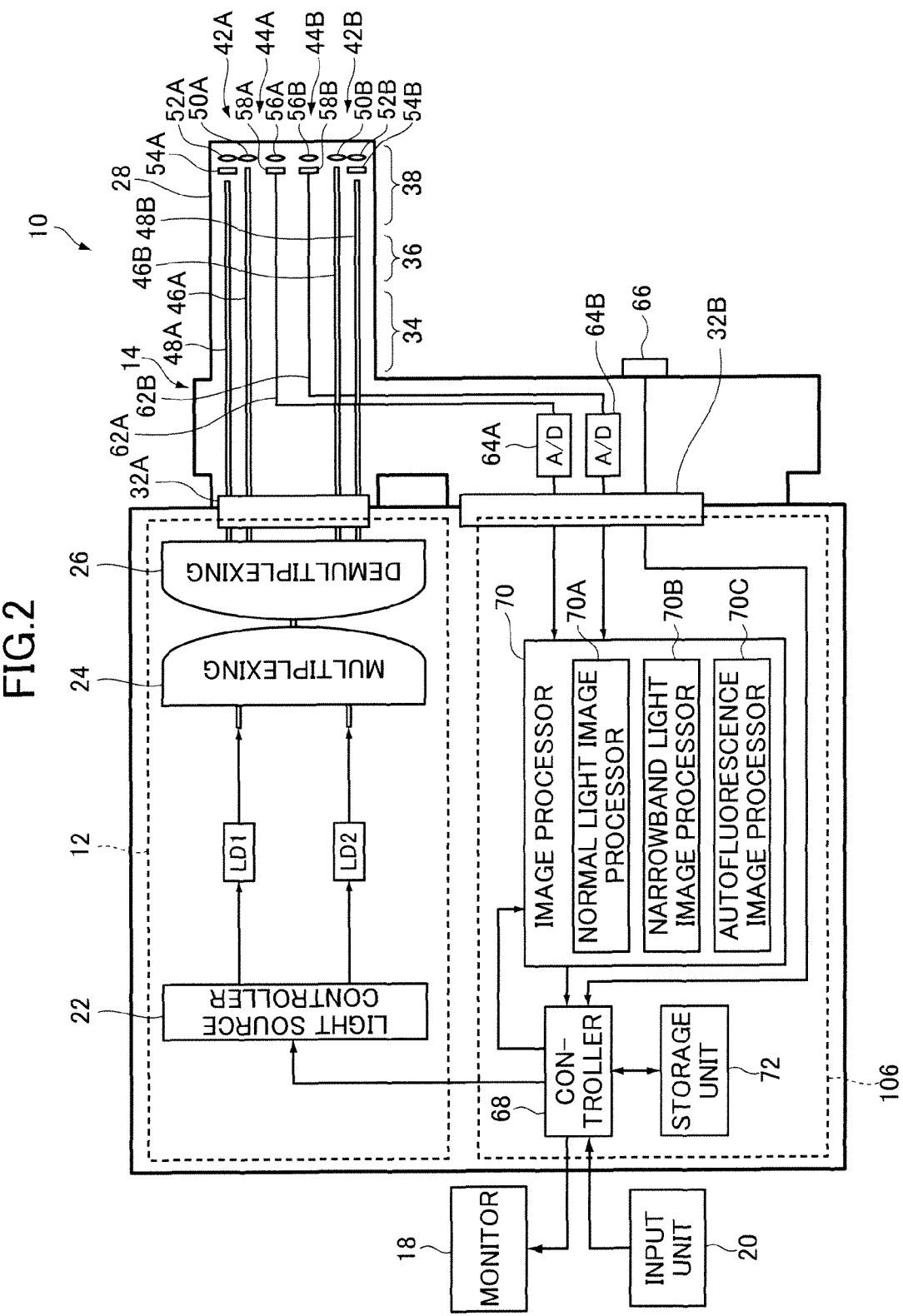
FIG. 2 is a block diagram illustrating an internal configuration of the endoscopic diagnosis system of FIG. 1.

FIG. 1 is an external view of an embodiment illustrating a configuration of the endoscopic diagnosis system according to the invention; FIG. 2 is a block diagram illustrating an internal configuration thereof. A endoscopic diagnosis system 10 illustrated in these figures comprises a light source device 12 for emitting a plurality of light having different ranges of wavelength; an endoscope device 14 for guiding light emitted from the light source device 12 to illuminate a subject's region under observation with the illumination light and imaging the reflected light or an autofluorescence from the subject; a processor 16 for image-processing the acquired image acquired by the endoscope device 14 and outputting an endoscopic image; a monitor 18 for displaying an endoscopic image outputted from the processor 16; and an input unit 20 for receiving input operations.

The endoscopic diagnosis system 10 is capable of normal light observation mode for illuminating the subject with normal light and imaging the reflected light thereof to display (observe) a normal light image and special light observation mode (narrowband light observation mode, a first autofluorescence observation mode, and a second autofluorescence observation mode) for illuminating the subject with special light and imaging the reflected light or autofluorescence to display a special light image (a narrowband light image, a first autofluorescence image, and a second autofluorescence image). The observation mode is switched as appropriate according to an instruction entered by a selector switch 66 of the endoscope device 14 or the input unit 20.

The observation mode is not limited to normal light observation mode and special light observation mode selected as above and may alternatively be freely switched among the normal light observation mode and the special light observation mode including the narrowband light observation mode, the first autofluorescence observation mode, and the second autofluorescence observation mode.

The light source device 12 comprises a light source controller 22, two kinds of laser light sources LD1, LD2 for emitting laser beams having different wavelength ranges, a combiner (multiplexer) 24, and a coupler (demultiplexer) 26.

According to this embodiment, the laser light sources LD1, LD2 emit narrowband light beams having given wavelength ranges with different central wavelengths of 405 nm and 445 nm (e.g., central wavelength+/−10 nm), respectively. The laser light source LD1 is provided to acquire a narrowband light image and a first autofluorescence image; the laser light source LD2 is provided to acquire a normal light image and a second autofluorescence image.

As described later, the laser light source LD2 generates excitation light for normal light observation to cause a fluorescent body to generate white light (pseudo white light). The white light source (normal light source) for generating white light is not limited to a light source using a combination of excitation light and fluorescent body and may be any light source to generate white light, including, for example, a xenon lamp, a halogen lamp, and a white LED (light emitting diode). The white light source may use separate light sources for acquiring the normal light image and for acquiring the second autofluorescence image. The laser beams emitted from the laser light sources LD1, LD2 are not limited in wavelength to the above; laser beams capable of serving the same purpose may be selected as appropriate.

The on/off control and light amount control of the laser light sources LD1, LD2 are made independently between these light sources by the light source controller 22 that is controlled by a controller of the processor 16 described later, and the emission timing and the emission amount ratio of the laser light sources LD1, LD2 can be freely varied.

The laser light sources LD1, LD2 may be constituted using, among others, broad area type InGaN-based laser diodes as well as InGaNas-based laser diodes and GaNas-based laser diodes.

The light source controller 22 turns the laser light source LD1 off and turns the laser light source LD2 on in the normal light observation mode. In the special light observation mode, the light source controller 22 switches the observation mode among the narrowband light observation mode, the first autofluorescence observation mode, and the second autofluorescence observation mode in this order in the special light observation mode every frame time. The switching may be made once in a plurality of frames in lieu of every frame. The light source controller 22 turns on both laser light sources LD1, LD2 in the narrowband light observation mode, turns on the laser light source LD1 and turns off the laser light source LD2 in the first autofluorescence observation mode, and turns off the laser light source LD1 and turns on the laser light source LD2 in the second autofluorescence observation mode. In the first and the second autofluorescence observation mode, the light source controller 22 supplies the laser light sources LD1, LD2 each with a drive current twice as great as that in the narrowband light observation mode to increase their emission amounts so as to be double the emission amounts in the narrowband light observation mode.

The laser beams emitted from the laser light sources LD1, LD2 are passed through condenser lenses (not shown) to enter their respective optical fibers, combined by the combiner 24 and divided into four channels of light beams by the coupler 26 before being transmitted to a connector unit 32A. The combiner 24 and the coupler 26 are composed of, for example, a half mirror or a reflection mirror. The configuration is not thereto, however; the laser beams from the laser light sources LD1, LD2 may be directly transmitted to the connector unit 32A in lieu of through the combiner 24 and the coupler 26.

The endoscope device 14 is an electronic endoscope instrument comprising an optical system for illumination for emitting four channels (four beams) of illumination light from the tip of the endoscope insertion section inserted into the inside of the subject's body and two channels (two sensors) of optical imaging system for acquiring an endoscopic image of the region under observation. The endoscope device 14 comprises the endoscope insertion section 28, an operating unit 30 for bending the tip of the endoscope insertion section 28 and performing observation operations, and connector units 32A, 32B for detachably connecting the endoscope device 14 to the light source device 12 and the processor 16.

The endoscope insertion section 28 comprises a flexible portion 34 having a flexibility, a bending portion 36, and a tip 38 (also referred to below as tip of the endoscope).

The bending portion 36 is provided between the flexible portion 34 and the tip 38 and is so configured as to be bendable by rotating an angle knob 40 provided on the operating unit 30. The bending portion 36 can be bent in any direction and to any angle according to, for example, the subject's site for which the endoscope device 14 is used, so that the endoscope tip portion 38 may be directed toward a desired site for observation.

Figure 3:
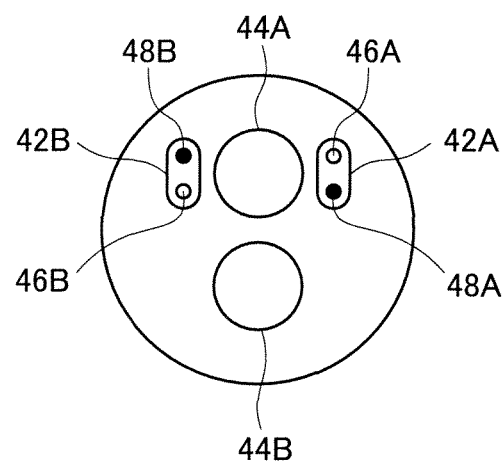
FIG. 3 is a conceptual view illustrating a tip portion of an endoscope insertion section of the endoscopic diagnosis system of FIG. 1.

At the tip end surface of the endoscope tip portion 38 are provided two channels of illumination windows 42A, 42B for illuminating a region under observation and two channels of observation windows 44A, 44B for imaging the reflected light or autofluorescence from the region under observation as illustrated in FIG. 3.

On the inside of the illumination window 42A are provided two channels of optical fibers 46A, 48B. The optical fibers 46A, 48B extend from the light source device 12 through the connector unit 32A to the scope tip portion 38. The optical fiber 46A has at its tip portion (its end closer to the illumination window 42A) an optical system including, for example, a lens 50A. The optical fiber 48A has at its tip portion a fluorescent body 54A, and beyond the fluorescent body 54A is provided an optical system including, for example, a lens 52A.

On the inside of the illumination window 42B are likewise provided two channels of optical fibers: an optical fiber 46B having at its tip portion an optical system including, for example, a lens 50B; and an optical fiber 48B having at its tip portion an optical system including, for example, a fluorescent body 54B and a lens 52B.

As illustrated in FIG. 3, the illumination windows 42A, 42B are located on opposite sides of the observation window 44A in the endoscope tip portion 38. The optical fibers 46A, 46B are located on opposite sides of the observation window 44A so that a line connecting both of them intersects the observation window 44A; the optical fibers 48A, 48B are located on opposite sides of the observation window 44A so that the line connecting the optical fibers 46A, 46B intersects a line connecting the optical fibers 48A, 48B in the observation window 44A. The optical fibers 46A, 46B located across from each other emit the same kind of illumination light (excitation light for autofluorescence observation or narrowband light) while the optical fibers 48A, 48B emit the same kind of illumination light (white light), thus preventing uneven illumination.

Fluorescent bodies 54A, 54B comprise a plurality of kinds of fluorescent substances that emit green to yellow light when excited upon absorbing part of the blue laser beam emitted from the laser light source LD2 (e.g., YAG-based fluorescent substance or BAM ($BaMgAl_{10}O_{17}$)-based fluorescent substance. When the excitation light for normal light observation illuminates the fluorescent bodies 54A, 54B, the green to yellow excited luminescence light (fluorescence) emitted from the fluorescent bodies 54A, 54B blends with part of the blue laser beam that is transmitted without being absorbed by the fluorescent bodies 54A, 54B to generate white light (pseudo white light).

Figure 4:
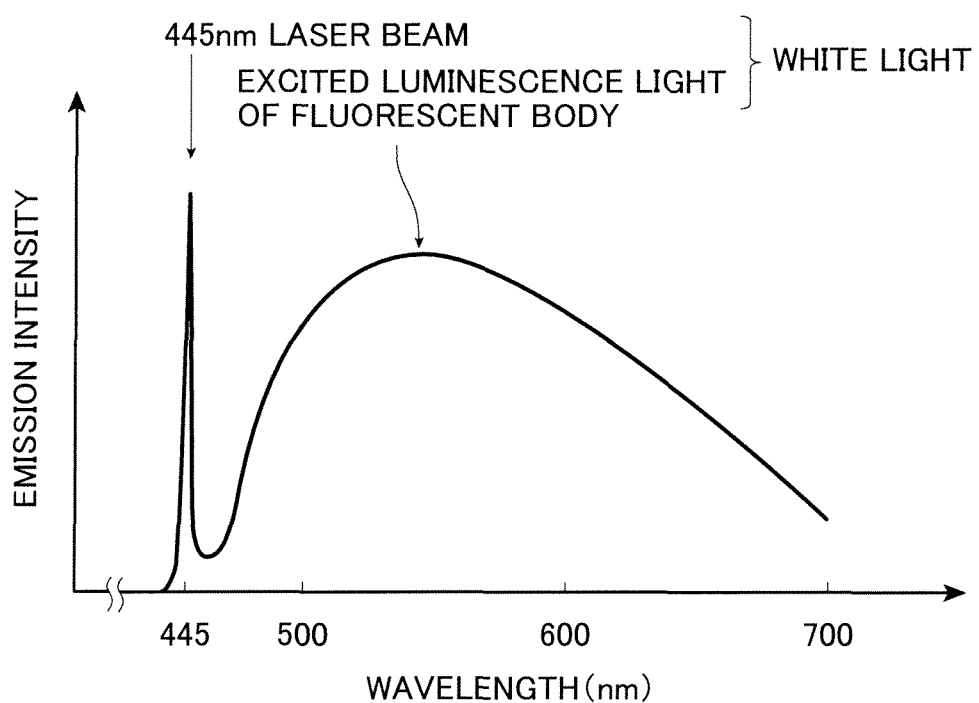
FIG. 4 is a graph illustrating an emission spectrum of a blue laser beam emitted from a blue laser light source and light obtained through wavelength conversion of blue laser beam by a fluorescent body.

FIG. 4 shows a graph illustrating an emission spectrum of the blue laser beam emitted from a blue laser light source and of light obtained through wavelength conversion of the blue laser beam by a fluorescent body. The blue laser beam emitted from the laser light source LD2 is represented by an emission line having a central wavelength of 445 nm; the excited luminescence light excited by the blue laser beam and emitted from the fluorescent bodies 54A, 54B has a spectral intensity distribution such that the light emission intensity increases in a wavelength range of about 450 nm to 700 nm. The excited luminescence light and the blue laser beam combine to produce pseudo white light as described above.

For the purpose of the invention, the white light is not limited to light containing strictly all the wavelength components of visible light but need only contain light having a specific wavelength range such as, for example, light having reference colors such as red, green, and blue, as well as the above pseudo white light. Thus, the white light herein broadly also includes, for example, light containing wavelength components corresponding to green to red light and light containing wavelength components corresponding to blue to green light The optical system for illumination comprising the illumination window 42A and the optical system for illumination comprising the illumination window 42B each have an equivalent configuration and an operation, so that the illumination windows 42A, 42B basically emit equal illumination light simultaneously. The illumination windows 42A, 42B may emit different illumination light. Provision of optical systems for illumination that emit four channels of illumination light is not essential; an optical systems for illumination to emit two or one channel of illumination light, for example, may be used to achieve an equivalent function.

On the inside of the observation window 44A is installed an optical system including, for example, an object lens unit 56A for introducing image light from the subject's region under observation and, further behind the object lens unit 56A is installed an image sensor 58A (first image sensor) such as a CCD (Charge Coupled Device) image sensor and a CMOS (Complementary Metal-Oxide Semiconductor) image sensor for acquiring image information on the subject's region under observation. Similarly, behind the observation window 44B is installed an optical system including, for example, an object lens unit 56B; behind the object lens unit 56B is provided an image sensor 58B (second image sensor). The image sensor 58A is provided for normal light observation and narrowband light observation; the image sensor 58B is provided for autofluorescence observation.

Figure 5:
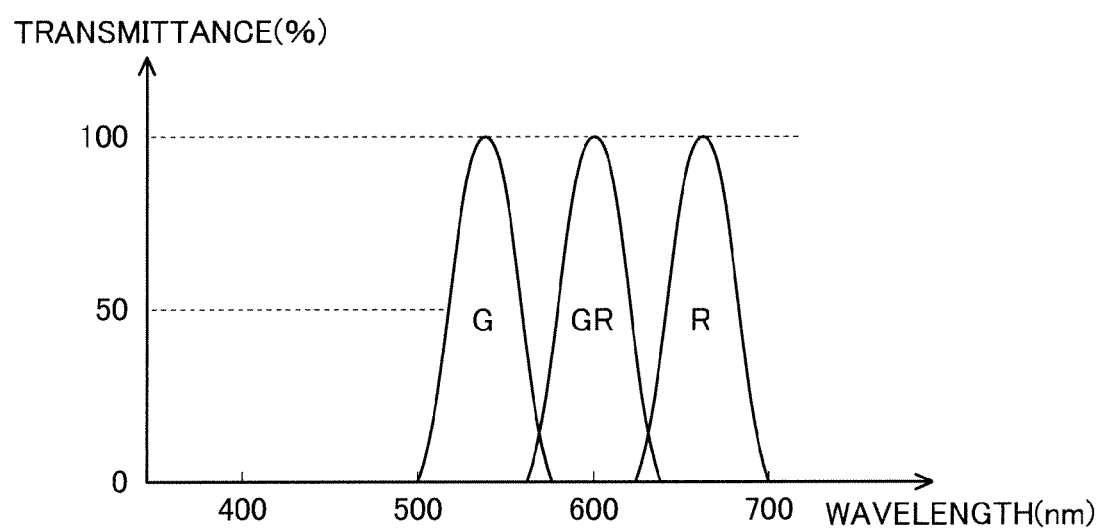
FIG. 5 is a graph illustrating spectral transmittances of red, green and red, and red color filters dividing a wavelength range of about 500 nm to 700 nm of red and green light, which is an emission wavelength range of autofluorescence, into three ranges.

The image sensors 58A, 58B receive light from the object lens units 56A, 56B with a light receiving surface (imaging surface), photoelectrically convert the received light into imaging signals (analog signals), and output the imaging signals. The receiving surface of the image sensor 58A is provided with red, green, and blue color filters having spectral transmittances dividing a wavelength range of about 370 nm to 720 nm of visual light into three ranges; a red pixel, a green pixel, and a blue pixel forming one set of pixels, a plurality of sets of pixels are arranged in the form of matrix. As illustrated in FIG. 5, the receiving surface of the image sensor 58B is provided with red, green and red, and green color filters having spectral transmittances dividing a wavelength range of about 500 nm to 700 nm of red and green light, which is an emission wavelength range of the autofluorescence, into three ranges. The color filters of the image sensor 58B have equivalent transmittance characteristics as shown in FIG. 4 in JP 2007-50106 A.

Because the fluorescence intensity of autofluorescence is feeble, the image sensor 58B used for the autofluorescence observation preferably has a higher sensitivity than the image sensor 58A for the normal light observation and the narrowband light observation.

The light emitted from the light source device 12 and guided through the optical fibers 46A, 46B and 48A, 48B is emitted from the endoscope tip portion 38 toward the subject's region under observation. The region under observation illuminated by the illumination light is imaged on the light receiving surfaces of the image sensors 58A, 58B through the object lens units 56A, 56B, and undergoes photoelectric conversion by the image sensors 58A, 58B to obtain an image. The image sensors 58A, 58B output imaging signals (analog signals) of the subject's imaged region under observation.

The imaging signal (analog signal) of an image (normal light image and narrowband light image) outputted from the image sensor 58A and the imaging signal (analog signal) of an image (autofluorescence image) outputted from the image sensor 58B are inputted to A/D converters 64A, 64B via scope cables 62A, 62B. The A/D converters 64A, 64B convert the imaging signals (analog signals) supplied from the image sensors 58A, 58B to image signals (digital signals). The image signal obtained through the conversion passes through the connector unit 32B to enter an image processor of the processor 16.

In the normal light observation mode, the excitation light for the normal light observation emitted from the light source LD2 is guided through the optical fibers 48A, 48B to illuminate the fluorescent bodies 54A, 54B, whereupon the white light generated from the fluorescent bodies 54A, 54B is emitted from the illumination windows 42A, 42B to illuminate the subject's region under observation. The reflected light from the subject's region under observation illuminated by the white light is condensed by the object lens unit 56A, whereupon a normal light image is acquired by the image sensor 58.

In the narrowband light observation mode, in addition to the excitation light for the normal light observation, the narrowband light emitted from the laser light source LD1 is guided through the optical fibers 46A, 46B, and the white light and the narrowband light are simultaneously emitted from the endoscope tip portion 38 toward the subject's region under observation at a given emission ratio. The reflected light from the subject's region under observation illuminated by the white light and the narrowband light are condensed by the object lens unit 56A, whereupon a narrowband light image is acquired by the image sensor 58A. When only blood vessels lying in the superficial layer are to be observed, only narrowband light may be emitted without white light to acquire a narrowband light image.

In the autofluorescence observation mode (first and second autofluorescence observation mode), the excitation light for the autofluorescence observation emitted from the laser light source LD1 or LD2 is guided through the optical fibers 46A, 46B and emitted from the endoscope tip portion 38 toward the subject's region under observation. The autofluorescence emitted from the subject's region under observation illuminated by the excitation light is condensed by the object lens unit 56B, whereupon an autofluorescence image (a first and a second autofluorescence image) are acquired by the image sensor 58B.

The relationship between the excitation light for autofluorescence observation and autofluorescent substance will now be described.

Figure 9:
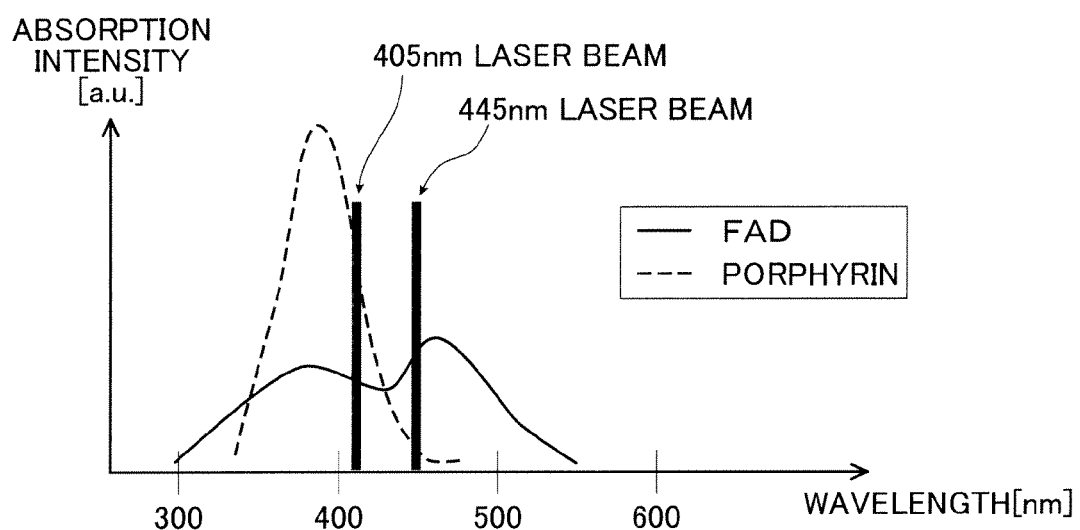
FIG. 9 is a graph of an example of light absorption intensity characteristics of autofluorescent substances.

FIG. 9 is a graph of an example of light absorption intensity characteristics of autofluorescent substances. In the graph, the vertical axis shows light absorption intensity of autofluorescent substances (a.u.: any unit), and the horizontal axis shows wavelength (nm). The graph shows absorption intensity characteristics of FAD (Flavin Adenine Dinucleotide) and porphyrin, both autofluorescent substances. The graph also shows central wavelengths 405 nm and 445 nm of laser beams used as excitation light for the autofluorescence observation in this embodiment.

FAD has characteristics to absorb light having a wavelength range of about 270 nm to 540 nm. The light absorption intensity of FAD gradually increases as the wavelength increases from about 270 nm, then reaches a first peak at a wavelength of about 380 nm and thereafter gradually decreases as the wavelength increases, reaching a minimum at a wavelength of about 420 nm. The absorption intensity then gradually increases again as the wavelength increases from about 420 nm and reaches a second peak at a wavelength of about 460 nm, thereafter gradually decreasing as the wavelength increases.

Porphyrin has characteristics to absorb light having a wavelength range of about 340 nm to 450 nm. Porphyrin has light absorption intensity characteristics peaking at a wavelength of about 390 nm and gradually decreasing as the wavelength decreases or increases.

Thus, in the first autofluorescence observation mode, illumination of the subject with a laser beam having a central wavelength of 405 nm enables excitation of both FAD and porphyrin in the region under observation to generate autofluorescence. In the second autofluorescence observation mode, illumination of the subject with a laser beam having a central wavelength of 445 nm enables excitation of mostly FAD in the region under observation to generate autofluorescence.

Figure 10:
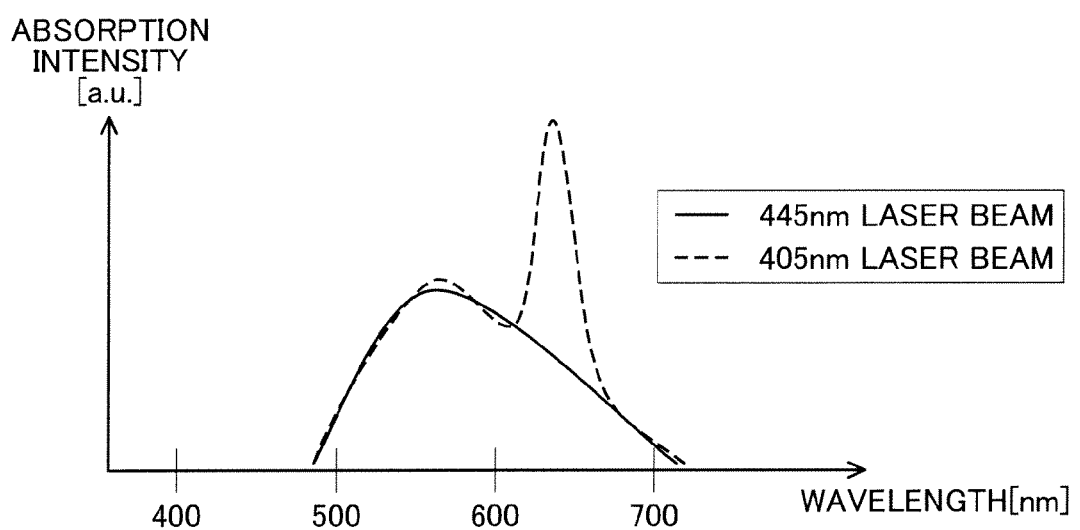
FIG. 10 is a graph of an example of fluorescence intensities autofluorescent substances.
Figure 11:
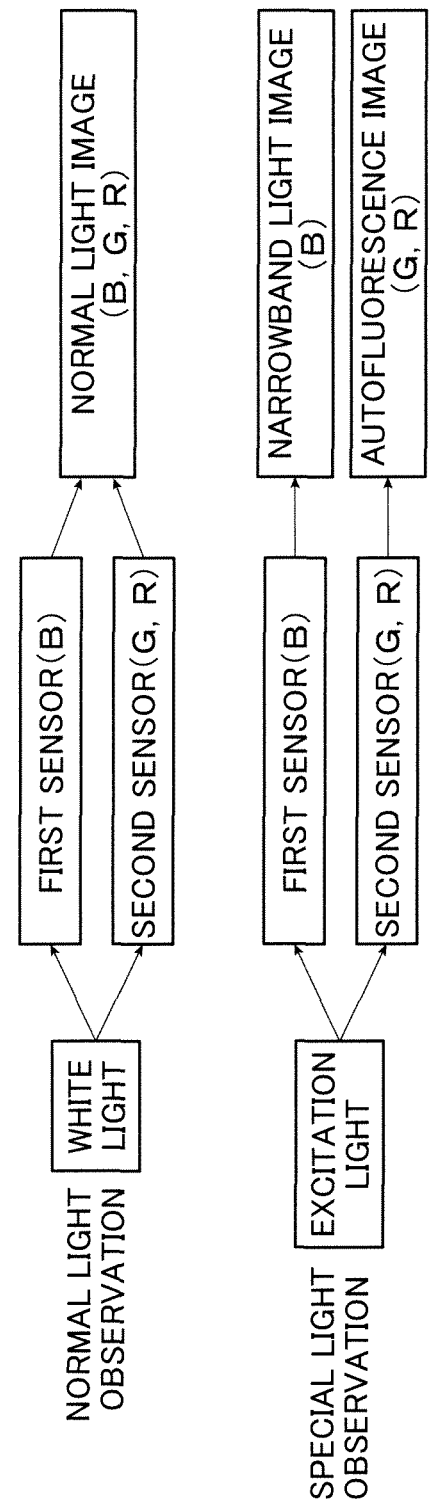
FIG. 11 is a conceptual view of an example illustrating processing performed by a conventional endoscopic diagnosis system in respective observation modes.

FIG. 10 is a graph of an example of fluorescence intensity characteristics of autofluorescent substances. In the graph, the vertical axis shows fluorescence intensity of autofluorescent substances (a.u.), and the horizontal axis shows wavelength (nm). The graph, corresponding to the graph of FIG. 9, shows a fluorescence intensity distribution of autofluorescence emitted from an autofluorescent substance when the subject's region under observation is illuminated by laser beams having central wavelengths of 405 nm and 445 nm used as excitation light for the autofluorescence observation.

In the first autofluorescence observation mode, when a laser beam having a central wavelength of 405 nm is used as excitation light to illuminate the subject, the region under observation illuminated by the excitation light generates autofluorescence having a wavelength range of about 480 nm to 740 nm. The fluorescence intensity of the autofluorescence gradually increases as the wavelength increases from about 480 nm, reaches a first peak at a wavelength of about 560 nm and thereafter gradually decreases as the wavelength increases, reaching a minimum at a wavelength of about 610 nm. The fluorescence intensity then gradually increases again as the wavelength increases from about 610 nm and reaches a second peak at a wavelength of about 630 nm, thereafter gradually decreasing as the wavelength increases. The autofluorescent substance representing part of the characteristics curve near the first peak is mostly FAD while the autofluorescent substance representing part of the characteristics curve near the second peak is mostly porphyrin.

In the second autofluorescence observation mode, when a laser beam having a central wavelength of 445 nm illuminates the subject as excitation light, the region under observation illuminated by the excitation light generates autofluorescence having a wavelength range of about 480 nm to 720 nm. The autofluorescence has fluorescence intensity characteristics peaking at a wavelength of about 560 nm and gradually decreasing as the wavelength decreases or increases. The autofluorescent substance representing the characteristics curve in this case is mostly FAD.

Thus illumination of the subject's region under observation with laser beams having two different central wavelengths, specifically 405 nm and 445 nm, as excitation light makes it possible to excite both FAD and porphyrin or mostly FAD and generate autofluorescence, thereby obtaining autofluorescence distributions exhibiting respective characteristics of FAD and porphyrin. Thus, changing the central wavelength of the excitation light for the autofluorescence observation enables selective excitation of a specific autofluorescent substance.

The operating unit 30 and the endoscope insertion section 28 contain various channels such as a forceps channel for inserting, for example, a tissue collecting tool and air supply/water supply channels, not shown.

The processor 16 comprises the controller 68, the image processor 70, and a storage unit 72. The controller 68 is connected to the monitor 18 and the input unit 20. The processor 16 controls the light source controller 22 of the light source device 12 according to an instruction inputted from the selector switch 66 of the endoscope device 14 and the input unit 20, image-processes an image signal inputted from the endoscope device 14, and produces and outputs a display image to the monitor 18.

The controller 68 controls the operations of the image processor 70 and the light source controller 22 of the light source device 12 according to instructions given by the selector switch 66 of the endoscope device 14 and the input unit 20, such as, for example, an observation mode instruction.

The image processor 70 performs a given image processing on the image signal entered from the endoscope device 14 according to the observation mode under the control by the controller 68 depending on the kinds of images including a normal light image, a narrowband light image, and an autofluorescence image. The image signal processed by the image processor 70 is supplied to the controller 68, which produces an endoscopic observation image from this processed image and other information. The endoscopic observation image is displayed on the monitor 18 and, where necessary, stored in the storage unit 72 composed of a memory or a storage device.

The image processor 70 comprises a normal light image processor 70A, a narrowband light image processor 70B, and an autofluorescence image processor 70C. In the normal light observation mode and the narrowband light observation mode, the image signal (image data) from the A/D converter 64A is supplied to the normal light image processor 70A and the narrowband light image processor 70B. In the autofluorescence observation mode, the image signal from the A/D converter 64B is supplied to the autofluorescence image processor 70C.

The normal light image processor 70A, the narrowband light image processor 70B, and the autofluorescence image processor 70C perform given image processing suited to respective endoscopic images on the image signals of the normal light image, the narrowband light image, and the autofluorescence image, respectively, in the normal light observation mode, the narrowband light observation mode, and the autofluorescence observation mode to output (produce) a normal light image signal (normal light image), a narrowband light image signal (narrowband light image), and an autofluorescence image signal (autofluorescence image).

Figure 6:
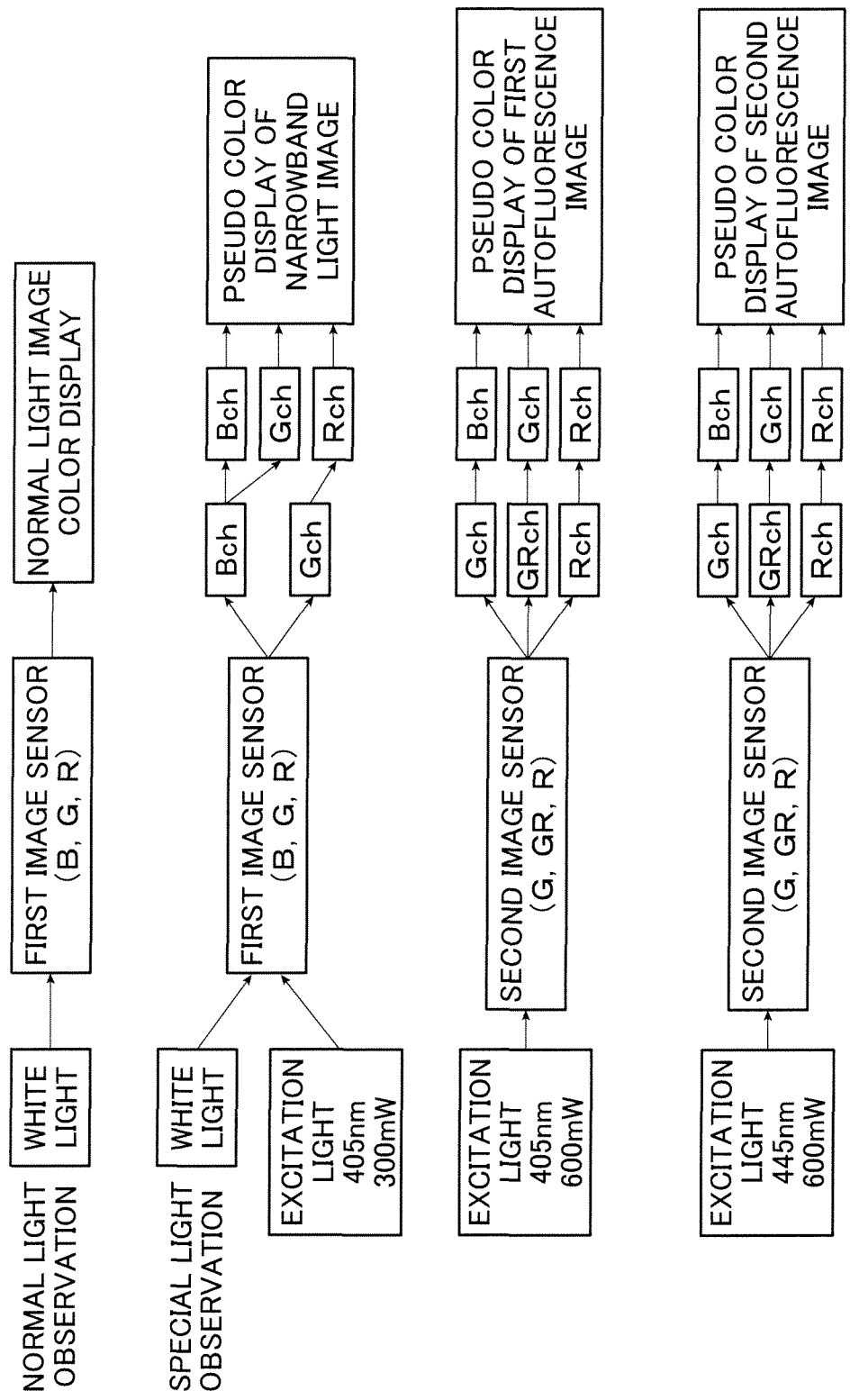
FIG. 6 is a conceptual view illustrating processing performed by the endoscopic diagnosis system of FIG. 1 in respective observation modes.

As illustrated in the conceptual view of FIG. 6, the normal light image processor 70A uses the red, the green, and the blue channel (pixels) of image data (image signals) of the normal light image to output the normal light image signals for color display of the normal light image in the normal light observation mode.

The narrowband light image processor 70B assigns the blue channel of image data of the narrowband light image to the blue and the green channel and assigns the green channel of image data to the red channel in the narrowband light observation mode to output the narrowband light image signals for pseudo color display of the narrowband light image.

The autofluorescence image processor 70C assigns the green channel of image data of the autofluorescence image to the blue channel, assigns the green and the red channel of image data to the green channel, and assigns the red channel of image data to the red channel in the autofluorescence observation mode to output the autofluorescence image signal for pseudo color display of the autofluorescence image. Because the intensity of the autofluorescence is feeble, the autofluorescence image processor 70C performs a given signal amplification processing.

The normal light image signal, the narrowband light image signal, and the autofluorescence image signal are stored in a storage unit 72 by unit of, for example, one sheet (frame) of image.

The image processor 70 outputs the normal light image signal, the narrowband light image signal, and the autofluorescence image signal, which are inputted to the controller 68. The controller 68 causes one of the normal light image, the narrowband light image, and the autofluorescence image to be displayed on the monitor 18 based on the narrowband light image signal, the normal light image signal, and the autofluorescence image signal according to the observation mode.

Figure 7:
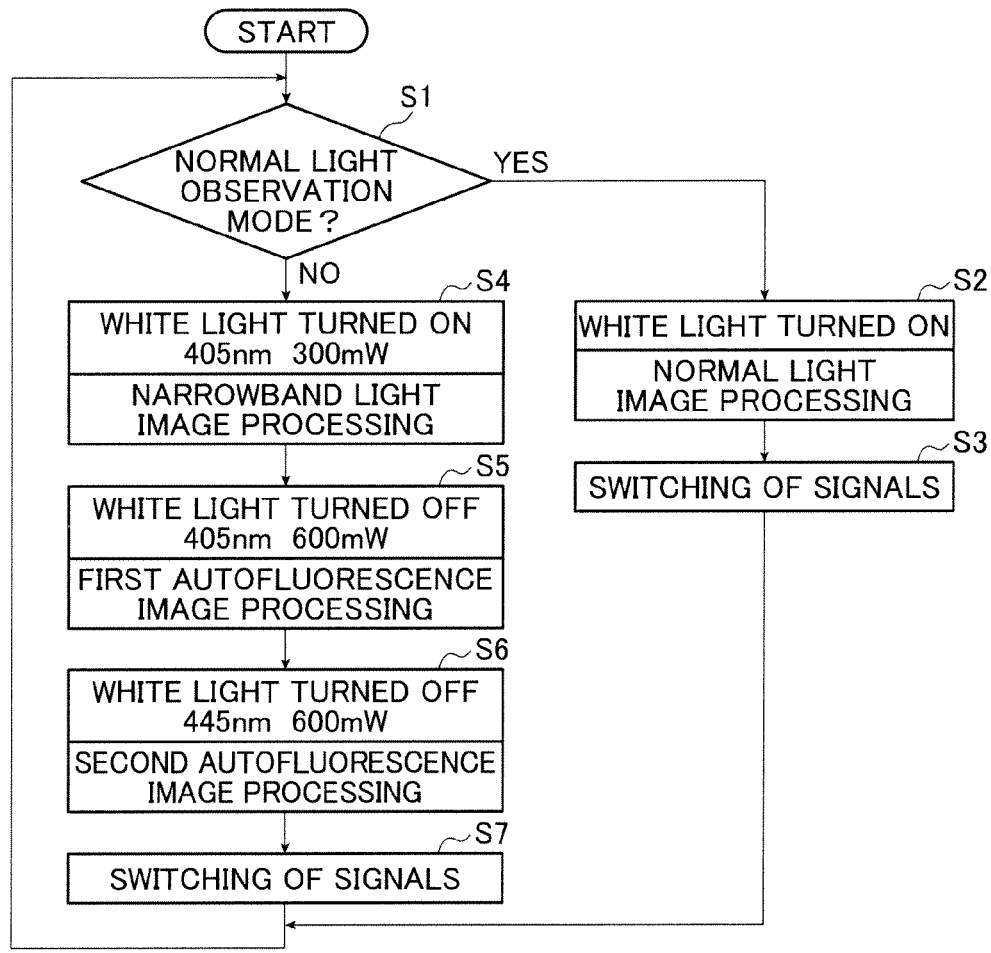
FIG. 7 is a flow chart illustrating an operation of the endoscopic diagnosis system of FIG. 1.

The operation of the endoscopic diagnosis system 10 will now be described referring to the conceptual view of FIG. 6 and the flowchart of FIG. 7.

First, the controller 22 judges whether the observation mode is the normal light observation mode in step S1.

When the observation mode is judged to be the normal light observation mode in step S1 (YES in step S1), the light source controller 22 causes the laser light source LD1 to be turned off and the laser light source LD2 to be turned on in step S2. The laser beam having a central wavelength of 445 nm emitted from the laser light source LD2 illuminates the fluorescent bodies 54A, 54B, and the white light emitted from the fluorescent bodies 54A, 54B illuminates the subject, whereupon the reflected light thereof is received by the image sensor 58A (first image sensor) to acquire the normal light image. The normal light image is displayed based on the blue, green, and red image data of the normal light image as illustrated in FIG. 6 through normal light image processing.

Subsequently, when the observation mode is switched (signal switching) in step S3, the procedure returns to step S1.

Figure 8:
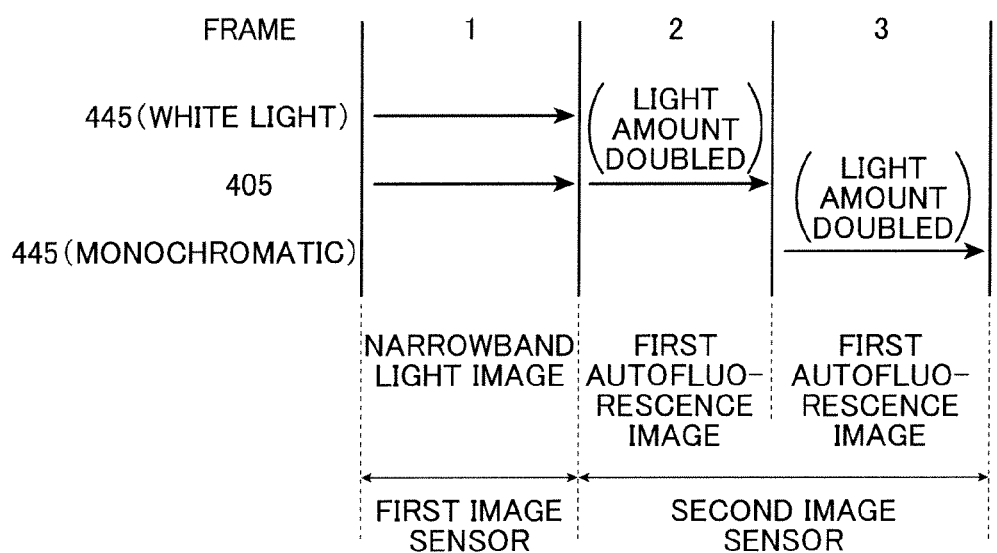
FIG. 8 is a conceptual view of an example illustrating an operation in special light observation mode in the endoscopic diagnosis system of FIG. 1.

When, on the other hand, the observation mode is judged not to be the normal light observation mode, or judged to be the special light observation mode (NO in step S1), the special light observation is sequentially carried out in the narrowband light observation mode, the first autofluorescence observation mode, and the second autofluorescence observation mode in this order under the control of the controller 68 every one frame time as illustrated in FIG. 8.

First, in the narrowband light observation mode, the light source controller 22 controls both the laser light sources LD1, LD2 to be turned on in step S4. The laser beam having a central wavelength of 405 nm emitted from the laser light source LD1 and the white light excited by the laser beam having a central wavelength of 445 nm emitted from the laser light source LD2 and emitted from the fluorescent bodies 54A, 54B are allowed to simultaneously illuminate the subject at a given emission ratio, whereupon the reflected light thereof is received by the image sensor 58A (first image sensor) to acquire the narrowband light image. As illustrated in FIG. 6, the narrowband light image is displayed in pseudo color by assigning the blue channel of image data of the narrowband light image to the blue and the green channel and assigning the green channel of image data to the red channel.

In the narrowband light observation mode, blood vessels lying in the superficial to intermediate layer of the subject can be observed by illuminating the subject with the laser beam having a central wavelength of 405 nm and the white light at a given emission ratio.

Then, in the first autofluorescence observation mode, the light source controller 22 controls the laser light source LD1 to be turned on and the laser light source LD2 to be turned off in step S5. The laser light source LD1 is supplied with a drive current twice as great as that in the narrowband light observation mode (e.g., the output of the laser beam in the first autofluorescence observation mode is 600 mW for an output of 300 mW of the laser beam in the narrowband light observation mode), so that the emission amount of the laser beam emitted from the laser light source LD1 is double the emission amount in the narrowband light observation mode. The laser beam having a central wavelength of 405 nm emitted from the laser light source LD1 is allowed to illuminate the subject, whereupon the autofluorescence emitted from the subject (including, as described earlier, autofluorescence emitted from FAD and porphyrin) is received by the image sensor 58B (second image sensor) to acquire the first autofluorescence image. As illustrated in FIG. 6, the first autofluorescence image is displayed in pseudo color by assigning the green channel of image data of the first autofluorescence image to the blue channel, assigning the green and the red channel of image data to the green channel, and assigning the green channel of image data to the red channel (first autofluorescence image processing).

Subsequently, in the second autofluorescence observation mode, the light source controller 22 controls the laser light source LD1 to be turned off and the laser light source LD2 to be turned on in step S6. Similarly, the emission amount of the laser beam emitted from the laser light source LD2 is twice as great as that in the narrowband light observation mode. The laser beam having a central wavelength of 445 nm emitted from the laser light source LD2 is allowed to illuminate the subject, whereupon the autofluorescence emitted from the subject (including, as described earlier, autofluorescence that is emitted from FAD) is received by the image sensor 58B (second image sensor) to acquire the second autofluorescence image. The operation to follow is the same as in the first autofluorescence observation mode (second autofluorescence image processor).

As described above, in the autofluorescence observation mode, a high-quality autofluorescence image can be obtained by increasing the emission amount of the excitation light for autofluorescence observation so as to be double that used in the narrowband light observation mode. Because the image sensor 58B is provided with green, green and red, and red color filters for dividing a wavelength range of 500 nm to 700 nm into three ranges as described above, the excitation light can be cut off to prevent reception thereof and variation in color of the autofluorescence having a wavelength range of 500 nm to 700 nm can be accurately reproduced.

Variation of the laser beam emission amount need not necessarily be achieved by increasing the drive current of the laser beam. For example, an ND filter (neutral density filter) for shielding the light received by the image sensor 58A at a given light shielding rate may be used as follows: in the narrowband light observation mode, the light source controller 22 controls the ND filter to be positioned on the optical path so as to reduce light received by the image sensor 58A; in the autofluorescence observation mode, the ND filter is not positioned on the optical path of the image sensor 58B or, in other words, the light to be received by the image sensor 58B is not shielded to increase the emission amount of the excitation light. The emission amount of the excitation light may be alternatively increased by increasing the lighting time of the laser light source in the autofluorescence observation mode so as to be double that in the narrowband light observation mode. Increasing the emission amount in the autofluorescence observation mode so as to be double that in the narrowband light observation mode is not essential; the emission amount in the autofluorescence observation mode need only be increased so as to be greater than the emission amount in the narrowband light observation mode.

Subsequently, when the observation mode is switched in step S7, the procedure returns to step S1.

The present invention is basically as described above.

While the invention has been described above in detail, the invention is by no means limited to the above embodiments, and various improvements and modifications may of course be made without departing from the spirit of the present invention.

I claim:
1. An endoscopic diagnosis system, comprising:
a white light source for emitting white light;
a first narrowband light source for emitting first narrowband light having a given wavelength range;
a second narrowband light source for emitting second narrowband light having a wavelength range different from that of the first narrowband light;
a first image sensor for receiving reflected light of the first narrowband light illuminating a subject from the subject and acquiring a narrowband light image in a narrowband light observation mode;
a second image sensor for receiving first autofluorescence emitted from the subject as the first narrowband light illuminates the subject to acquire a first autofluorescence image in a first autofluorescence observation mode and receiving second autofluorescence emitted from the subject as the second narrowband light illu- minates the subject to acquire a second autofluorescence image in a second autofluorescence observation mode; and a light source controller for illuminating the subject with the white light and the first narrowband light at a given emission ratio in the narrowband light observation mode, and increasing emission amounts of the first and the second narrowband light in the first and the second autofluorescence observation modes to emission amounts greater than emission amounts used in the narrowband light observation mode, wherein the first image sensor receives reflected light of the white light illuminating the subject from the subject to acquire a normal light image in a normal light observation mode and receives reflected light of the white light and the first narrowband light illuminating the subject at a given emission ratio from the subject to acquire the narrowband light image in the narrowband light observation mode, wherein the second image sensor is provided with red, green and red, and green color filters having spectral transmittances dividing light having a wavelength range of red and green light into three ranges, wherein an image processor assigns a green channel of image data of an autofluorescence image from the second image sensor to a blue channel, assigns a green and a red channel of image data from the second image sensor to a green channel, and assigns a red channel of image data from the second image sensor to a red channel in the first autofluorescence observation mode, to output an autofluorescence image signal for pseudo color display of the autofluorescence image, wherein the white light source comprises a third narrowband light source for emitting third narrowband light having a given wavelength range and a fluorescent body for emitting excited luminescence light when illuminated by the third narrowband light, so that the third narrowband light and the excited luminescence light generate pseudo white light, and wherein the white light source uses the second narrowband light source as the third narrowband light source.

2. The endoscopic diagnosis system according to claim 1, wherein the first narrowband light has a wavelength range of 405 nm+/−10 nm, and the second narrowband light has a wavelength range of 445 nm+/−10 nm.

3. The endoscopic diagnosis system according to claim 1, wherein the first autofluorescence contains autofluorescence emitted from Flavin Adenine Dinucleotide (FAD) and porphyrin, and the second autofluorescence contains autofluorescence emitted from FAD.

4. The endoscopic diagnosis system according to claim 1, wherein the first and the second narrowband light sources comprise laser light sources, and wherein the light source controller increases the emission amounts by increasing drive currents of the laser light sources in the first and the second autofluorescence observation modes so as to be greater than drive currents in the narrowband light observation mode.

5. The endoscopic diagnosis system according to claim 1, further comprising a light shielding filter for shielding light received by the first image sensor at a given shielding rate, wherein the light source controller increases the emission amounts by shielding light received by the first image sensor with the light shielding filter in the narrowband light observation mode and by not shielding light received by the second image sensor with the light shielding filter in the first and the second autofluorescence observation modes.

6. The endoscopic diagnosis system according to claim 1, wherein the light source controller increases the emission amounts by increasing a lighting time of the first and the second narrowband light source a source in the first and the second autofluorescence observation modes so as to be longer than a lighting time in the narrowband light observation mode.

7. The endoscopic diagnosis system according to claim 1, wherein the light source controller increases emission amounts of the first and the second narrowband light in the first and the second autofluorescence observation modes so as to be double emission amounts used in the narrowband light observation mode.

8. The endoscopic diagnosis system according to claim 1, wherein the light source controller switches the observation mode among the narrowband light observation mode, the first autofluorescence observation mode, and the second autofluorescence observation mode, in this order, in a special light observation mode in every predetermined time.

9. The endoscopic diagnosis system according to claim 1, wherein the first image sensor comprises a single image sensor that acquires the normal light image in the normal light observation mode and the narrowband light image in the narrowband light observation mode.

10. The endoscopic diagnosis system according to claim 1, wherein the first image sensor comprises a single image sensor.

* * * * *